United States Patent [19]

Nohira et al.

[11] Patent Number: 4,904,822
[45] Date of Patent: Feb. 27, 1990

[54] PROCESS FOR THE OPTICAL RESOLUTION OF (+)-2-HYDROXY-4-PHENYLBUTANOIC ACID

[75] Inventors: Hiroyuki Nohira, Urawa; Shinichi Yoshida, Misato, both of Japan

[73] Assignee: Kuraray Co., Ltd., Kurashiki, Japan

[21] Appl. No.: 307,948

[22] Filed: Feb. 9, 1989

[30] Foreign Application Priority Data

Feb. 19, 1988 [JP] Japan .................. 63-38273

[51] Int. Cl.$^4$ .............................. C07B 55/00
[52] U.S. Cl. .................... 562/401; 562/470
[58] Field of Search ............... 562/401, 470; 260/501.17

[56] References Cited

U.S. PATENT DOCUMENTS 3,725,437  4/1973  Nagoya et al. ............ 562/470
3,867,434  2/1975  Diamond .................... 562/470

FOREIGN PATENT DOCUMENTS

A2271868  6/1988  European Pat. Off. .
2047839  4/1971  Fed. Rep. of Germany .
2490491  3/1982  France .

OTHER PUBLICATIONS

Chemical Abstracts, vol. 109, No. 3, Jul. 18, 1988, Columbus, Ohio, U.S.A., M. Hashimoto "Preparation of Arylhydroxyalkanoic Acid Derivatives as Intermediates for Pharmaceuticals", p. 584, col. 2, abstract No. 22 654n & Jpn. Kodai tokkyo Koho JP 62, 212 329.

Primary Examiner—Paul J. Killos
Attorney, Agent, or Firm—Oblon, Spivak, McClelland, Maier & Neustadt

[57] ABSTRACT

A process for the optical resolution of (±)-2-hydroxy-4-phenylbutanoic acid which comprises treating (±)-2-hydroxy-4-phenylbutanoic acid with an optically active 1-(p-tolyl)ethylamine or an optically active N-(2-hydroxy)ethyl-α-methylbenzylamine as a resolving agent is provided by the present invention.

According to the invention, (−)-2-hydroxy-4-phenylbutanoic acid, which is useful as a starting substance for the synthesis of angiotensin converting enzyme-inhibiting pharmaceuticals, can especially be obtained in a highly pure state and in a high yield.

7 Claims, No Drawings

PROCESS FOR THE OPTICAL RESOLUTION OF (+)-2-HYDROXY-4-PHENYLBUTANOIC ACID

BACKGROUND OF THE INVENTION

1. Field of the Invention

The present invention relates to a process for optically resolving optically inactive 2-hydroxy-4-phenylbutanoic acid to obtain an active compound thereof.

2. Description of the Prior Art ($\pm$)-2-Hydroxy-4-phenylbutanoic acid is an important starting compound for synthesis of angiotensin converting enzyme-inhibiting pharmaceuticals such as Cilazapril, Benzapril, Quinapril, Enalapril, Ramipril, Lisinopril and 2-hydroxy-4-phenylbutanoic acid as prepared by chemical synthetic methods is generally obtained as an optically inactive racemate, i.e. ($\pm$)-carboxylic acid. However, pharmaceuticals derived from ($\pm$)-2-hydroxy-4-phenylbutanoic acid contained in ($\pm$)-2-hydroxy-4-phenylbutanoic acid have a much poorer inhibiting ability than that of pharmaceuticals derived from ($-$)-2-hydroxy-4-phenylbutanoic acid, and thus the development of a technique has hitherto been desired for effectively optically resolving ($\pm$)-2-hydroxy-4-phenylbutanoic acid to obtain highly pure ($-$)-2-hydroxy-4-phenylbutanoic acid.

Heretofore, as a method of obtaining an optically active 2-hydroxy-4-phenylbutanoic acid has been reported a method of obtaining the optically active compound by treating ($\pm$)-2-hydroxy-4-phenylbutanoic acid with an optically active method to form menthyl esters, repeating recrystallization from petroleum ether to obtain an optically active menthyl ester and hydrating it (Optical Resolution Procedures for Chemical Compounds pp. 476 (1981) published by OPTICAL RESOLUTION INFORMATION CENTER, Manhattan College, Riverdale, New York).

However, since the resolving agent used in this method is comparatively expensive and moreover the yield is not high of an optically active 2-hydroxy-4-phenylbutanoic acid obtained by resolution, there has been a problem that an optically active 2-hydroxy-4-phenylbutanoic acid cannot cheaply be supplied thereby.

SUMMARY OF THE INVENTION

It is accordingly an object of the invention to provide a process for optically resolving in a high purity, in a high yield and cheaply ($\pm$)-2-hydroxy-4-phenylbutanoic acid which is a starting substance for the synthesis of angiotensin converting enzyme-inhibiting pharmaceuticals. The above object of the invention has been accomplished by a process for the optical resolution of (-$\pm$)-2-hydroxy-4-phenylbutanoic acid which comprises treating ($\pm$)-2-hydroxy-4-phenylbutanoic acid with an optically active 1-(p-tolyl)ethylamine or an optically active N-(2-hydroxy)ethyl-$\alpha$-methylbenzylamine.

According to the process of the present invention, ($\pm$)-2-hydroxy-4-phenylbutanoic acid is optically resolved into ($\pm$)-2-hydroxy-4-phenylbutanoic acid and ($-$)-2-hydroxy-4-phenylbutanoic acid by forming due to the action of the above resolving agent diastereomer salts corresponding to ($\pm$)-2-hydroxy-4-phenylbutanoic acid and ($-$)-2-hydroxy-4-phenylbutanoic acid respectively and separating these diastereomer salts by utilization of the difference of solubilities thereof to the used solvent.

DESCRIPTION OF THE PREFERRED EMBODIMENT

In the invention, the molar ratio of optically active 1-(p-tolyl)ethylamine as a resolving agent to ($\pm$)-2-hydroxy-4-phenylbutanoic acid is not particularly restricted, but it is preferable to use the amine in an amount of 0.4 to 1 equivalent based on ($\pm$)-2-hydroxy-4-phenylbutanoic acid so that ($\pm$)-2-hydroxy-4-phenylbutanoic acid may be resolved in good efficiency and in a high purity. This 1-(p-tolyl)ethylamine is generally used in the presence of a solvent, and solvents usable for this purpose include, for example, $C_{1-6}$, preferably $C_{1-4}$ alkanols such as methanol, ethanol, 2-propanol, 1-propanol and 1-butanol, $C_{3-6}$ alkyl methyl ketones such as acetone and methyl isobutyl ketone, unsubstituted or methyl- or ethyl-substituted benzenes such as benzene, toluene and xylene, $C_{6-8}$ cycloalkanes such as cyclohexane, $C_{6-10}$ alkanes such as n-hexane, n-heptane, n-octane and n-decane, water, dioxane, tetrahydrofuran and tetrahydropyran and mixtures thereof. Above all, water dioxane and methyl isobutyl ketone are preferable as they can give an optically active 2-hydroxy-4-phenylbutanoic acid of a high purity. In case of using water as the solvent, it si preferable to neutralize the excess amount of ($\pm$)-2-hydroxy-4-phenylbutanoic acid with a base such as sodium hydroxide, potassium hydroxide, lithium hydroxide or ammonia because an optically active 2-hydroxy-4-phenylbutanoic acid of high purity can be obtained.

The amount of a solvent to be used is varied depending on kind of solvents, dissolution temperature or crystallization temperature and cannot be definitely prescribed, but may usually be selected from the range of 150 to 1500 ml per mole of 1-(p-tolyl)ethylamine. Preferred crystallization temperature is also varied depending on the amount of a solvent to be used, kind of solvent or dissolution temperature, but may usually be selected from the range of $-10°$ to $50°$ C. from an economical view.

In case of using an optically active N-(2-hydroxy)ethyl-$\alpha$-methylbenzylamine as the optical resolving agent, the molar ratio of the amine to ($\pm$)-2-hydroxy-4-phenylbutanoic acid is not particularly restricted. However, it is preferable to use the amine in an amount of 0.4 to 1.0 equivalent based on ($\pm$)-2-hydroxy-4-phenylbutanoic acid. N-(2-hydroxy)ethyl-$\alpha$-methylbenzylamine is generally used in the presence of a solvent, and solvents usable for this purpose include, for example, $C_{1-6}$, preferably $C_{1-4}$ alkanols such as methanol, ethanol, 2-propanol, 1-propanol and 1-butanol, $C_{3-6}$ alkyl methyl ketones such as acetone and methyl isobutyl ketone, unsubstituted or methyl- or ethylsubstituted benzenes such as benzene, toluene and xylene, $C_{6-8}$ cycloalkanes such as cyclohexane, $C_{6-10}$ alkanes such as n-hexane, n-heptane, n-octane and n-decane, water, dioxane, tetrahydrofuran and tetrahydropyran and mixtures thereof. Above all, unsubstituted or methyl- or ethylsubstituted benzenes, $C_{6-8}$ cycloalkanes, $C_{6-10}$ alkanes, and mixtures thereof, and water are preferable because they can give an optically active 2-hydroxy-4-phenylbutanoic acid of high purity. In case of using water as the solvent, it is preferable to neutralize the excess amount of ($\pm$)-2-hydroxy-4-phenylbutanoic acid with a base such as sodium hydroxide, potassium hydroxide, lithium hydroxide or ammonia because an optically active 2- hydroxy-4-phenylbutanoic acid of high purity can be obtained.

The amount of a solvent to be used is varied depending on kind of solvents, dissolution temperature or crystallization temperature and cannot be definitely prescribed, but may usually be selected from the range of 150 to 1500 ml per mole of N-(2-hydroxy)ethyl-α-methylbenzylamine. Preferred crystallization temperature is also varied depending on the amount of a solvent to be used, kind of the solvent or dissolution temperature, but may usually be selected from the range of −20° to 50° C. from an economical view.

The process of the present invention is carried out, for example, in the following manner. (±)-2-Hydroxy-4-phenylbutanoic acid and 0.4 to 1 equivalent, based on the (±)-2-hydroxy-4-phenylbutanoic acid, of optically active 1-(p-tolyl)ethylamine or N-(2-hydroxy)ethyl-α-methylbenzylamine are added to a solvent, followed by heating for dissolution. Subsequently, the solution is cooled to supersaturation. Preferably, a (±)-2-hydroxy-4-phenylbutanoic acid/(−)-1-(p-tolyl)ethylamine salt, (−)-2-hydroxy-4-phenylbutanoic acid/(±)-1-(p-tolyl)ethylamine salt, (±)-2-hydroxy-4phenylbutanoic acid/(±)-N-(2-hydroxy)ethyl-α-methylbenzylamine salt or (−)-2-hydroxy-4-phenylbutanoic acid/(−)-N-(2-hydroxy)ethyl-α-methylbenzylamine salt containing 1-(p-tolyl)ethylamine or N-(2-hydroxy)ethyl-α-methylbenzylamine in the same optically active form as that of the starting amine is added in a small amount, thereby permitting the same kind of sparingly soluble diastereomer salt to be deposited, followed by separation of this salt. The separation of the diastereomer salt may be effected by a method such as filtration or centrifugation.

The thus obtained diastereomer salt is treated with a base such as sodium hydroxide, potassium hydroxide or sodium methoxide, and (−) or (±) 1-(p-tolyl)ethylamine or (−) or (±) N-(2-hydroxy)ethyl-α-methylbenzylamine is recovered, followed by further treatment with an acid such as hydrochloric acid, sulfuric acid, phosphoric acid or p-toluenesulfonic acid to obtain (±) or (−) 2-hydroxy-4-phenylbutanoic acid. The above procedures may alternatively be carried out in the order of the acid treatment and optional subsequent base treatment.

The present invention is specifically described according to examples.

EXAMPLE 1

0.36 g (2 mmol) of (±)-2-Hydroxy-4-phenylbutanoic acid (hereinafter abbreviated as (±)-1) and 0.27 g (2 mmol) of (±)-1-(p-tolyl)ethylamine (hereinafter abbreviated as (±)-2) were added to 3.5 ml of dioxane and heated to form a solution, which was then gradually cooled to room temperature. After standing overnight, the deposited crystals were separated by filtration to obtain 0.18 g (0.58 mmol) of (−)-1/(±)-2 salt. The yield based on the employed (−)-1 was 58.0%, m.p. =148°-153° C. and $[\alpha]_{589}$ = +12.9° (C=1.1, methanol). 0.7 ml of a 1N sodium hydroxide solution was added to the salt, followed by ether extraction. 0.9 ml of 1N hydrochloric acid was added to the resulting aqueous layer, which was then extracted with ether. The organic layer was dried over anhydrous sodium sulfate and evaporated under reduced pressure to distil away the solvent, whereby 0.10 g (0.57 mmol) of (−)-1 was obtained. Yield 57.0%, m.p. =109°-112° C., $[\alpha]_{589}$ = −7.01° (C=0.9, 99% ethanol), optical purity 80.6%.

EXAMPLE 2

1.08 g (10 mmol) of (±)-1 and 1.08 g (8 mmol) of (±)-2 were added to 8 ml of dioxane and heated to form a solution, which was then gradually cooled to room temperature. After standing overnight, the deposited crystals were separated by filtration to obtain 0.97 g (3.08 mmol) of (−)-1/(±)-2 salt. The yield based on the employed (−)-1 was 61.6%, m.p. =145°-149° C., $[\alpha]_{589}$ = +11.1° (C=1.1, methanol). This salt was recrystallized from 2.7 ml of dioxane to obtain 0.80 g (2.53 mmol) of (−)-1/(±)-2 salt. The yield based on the employed (−)-1 was 50.6%, m.p. =149°-150° C., $[\alpha]_{589}$ = +13.5° (C=1.0, methanol). 3 ml of a 1N sodium hydroxide solution was added to the salt, followed by ether extraction. 4 ml of 1N hydrochloric acid was added to the resulting aqueous layer, which was then extracted with ether. The organic layer was dried over anhydrous sodium sulfate and evaporated under reduced pressure to distil away the solvent, whereby 0.45 g (2.51 mmol) of (−)-1 was obtained. Yield 50.2%, m.p. =111°-114° C., $[\alpha]_{589}$ = −8.21° (C=1.1, 99% ethanol),

EXAMPLE 3

5.41 g (30 mmol) of (±)-1 and 3.25 g (24 mmol) of (±)-2 were added to 24 ml of dioxane and heated to form a solution, which was then gradually cooled to room temperature. After standing overnight, the deposited crystals were separated by filtration to obtain 3.09 g (9.80 mmol) of (−)-1/(+)-2 salt. The yield based on the employed (−)-1 was 65.3%. m.p. =145°-148° C., $[\alpha]_{589}$ = +11.5° (C=1.5, methanol). This salt was recrystallized from 8.7 ml of dioxane to obtain 2.60 g (8.23 mmol) (−)-1/(+)-2 salt. The yield based on the employed (−)-1 was 54.9%. m.p. =149°-153° C., $[\alpha]_{589}$ = +12.7° (C=1.2, methanol). 9.6 ml of a 1N sodium hydroxide solution was added to the salt, followed by ether extraction. 1.9 ml of 6N hydrochloric acid was added to the resulting aqueous layer, which was then extracted with ether. The organic layer was dried over anhydrous sodium sulfate and evaporated under reduced pressure to distil away the solvent, whereby 1.47 g (8.17 mmol) of (−)-1 was obtained. Yield 54.5%, m.p. =111°-113° C., $[\alpha]_{589}$ = −8.27° (C=1.2, 99% ethanol), optical purity 95.1%.

EXAMPLE 4

0.60 g (2 mmol) of (±)-1 and 0.70 g (2 mmol) of (±)-2 were added to 1.3 ml of methyl isobutyl ketone and heated to form a solution, which was then gradually cooled to room temperature. After standing overnight, the deposited crystals were separated by filtration to obtain 0.24 g (0.76 mmol) of (−)-1/(+)-2 salt. This salt was recrystallized from 1.5 ml of methyl isobutyl ketone to obtain 0.17 g (0.55 mmol) of (−)-1/(±)-2 salt. The yield based on the employed (−)-1 was 55.0%, m.p. =146°-149° C., $[\alpha]_{589}$ = +13.0° (C=1.2, methanol). 1.5 ml of a 1N sodium hydroxide solution was added to the salt and the mixture was extracted with ether. 0.7 ml of 1N hydrochloric acid was added to the resulting aqueous layer, which was then extracted with ether. The organic layer was dried over anhydrous sodium sulfate and evaporated under reduced pressure to distil away the solvent, whereby 0.10 g (0.53 mmol) of (−)-1 was obtained. Yield 53.0%, m.p. =108°-111° C., $[\alpha]_{589}$ = −8.28° (C=0.9, 99% ethanol), optical purity 95.2%.

EXAMPLE 5

1.80 g (10 mmol) of (±)-1 and 1.08 g (8 mmol) of (±)-2 were added to 6 ml of methyl isobutyl ketone and heated to form a solution, which was then gradually cooled to room temperature. After standing overnight, the deposited crystals were separated by filtration to obtain 1.53 g (4.85 mmol) of (−)-1/(+)-2 salt. This salt was recrystallized from 7.0 ml of methyl isobutyl ketone to obtain 1.05 g (3.33 mmol) of (−)-1/(+)-2 salt. The yield based on the employed (−)-1 was 66.6%. m.p. =143°–151° C., $[\alpha]_{589} = +12.9°$ (C=1.0, methanol). 4.0 ml of a 1N sodium hydroxide solution was added to the salt, followed by ether extraction. 5.0 ml of 1N hydrochloric acid was added to the resulting water layer, followed by ether extraction. The organic layer was dried over anhydrous sodium sulfate and evaporated under reduced pressure to distil away the solvent, whereby 0.54 g (3.00 mmol) of (−)-1 was obtained. Yield 60.0%, m.p. =102°–108° C., $[\alpha]_{589} = -6.61°$ (C=1.1, 99% ethanol), optical density 76.0%.

EXAMPLE 6

1.80 g (10 mmol) of (±)-1- and 1.08 g (8 mmol) of (±)-2 were added to 8 ml of methyl isobutyl ketone and heated to form a solution, which was then gradually cooled to room temperature. After standing overnight, the deposited crystals were separated by filtration to obtain 1.16 g (3.67 mmol) of (−)-1/(+)-2 salt. This salt was recrystallized from 5.3 ml of methyl isobutyl ketone to obtain 0.95 g (3.00 mmol) of (−)-1/(±)-2 salt. The yield based on the employed (−)-1 was 60.0%. m.p. =147°–150° C., $[\alpha]_{589} = +14.0°$ (C=1.5, methanol). 3.6 ml of a 1N sodium hydroxide solution was added to the salt, followed by ether extraction. 4.3 ml of 1N hydrochloric acid was added to the resulting aqueous layer, which was then extracted with ether. The organic layer was dried over anhydrous sodium sulfate and the solvent was distilled away under reduced pressure to obtain 0.53 g (2.96 mmol) of (−)-1. Yield 59.2%, m.p.=110°–113° C., $[\alpha]_{589} = -7.17°$ (C=2.0, 99% ethanol), optical purity 82.4%.

EXAMPLE 7

450 g (2.5 mol) of (±)-1and 270 g (2.0 mol) of (±)-2 were added to 2000 ml of dioxane and heated to form a solution, which was then gradually cooled to room temperature. After standing for 24 hours, the deposited crystals were separated by filtration. These crystals were heated again with 700 ml of dioxane. The resulting solution was gradually cooled to room temperature and the deposited crystals were separated by filtration. This procedure was once repeated to obtain 313.9 g (0.997 mol) of (−)-1/(+)-2 salt. The yield based on (−)-1 was 79.8%. m.p. 153° C. 1200 ml of a 1N sodium hydroxide solution was added to the salt, followed by ether extraction. 1000 ml of 1N hydrochloric acid was added to the resulting aqueous layer, followed by ether extraction. The organic layer was dried over anhydrous sodium sulfate and ether was distilled away to obtain 174.72 g (0.971 mol) of (−)-1 salt. Yield 77.7%, $[\alpha]_{589} = -8.61°$ (C=1.0, 99% ethanol), optical purity 99%.

EXAMPLE 8

25.9 g (0.144 mol) of (±)-1 and 19.0 g (0.115 mol) of (−)-N-(2-hydroxyethyl)-α-methylbenzylamine (hereinafter abbreviated as (−)-3) were added to a mixed solvent of 74 ml of benzene and 31 ml of hexane and heated to form a solution. The solution was gradually cooled to room temperature and allowed to stand for 24 hours, and the deposited crystals were separated by filtration. These crystals were recrystallized from a mixed solvent of 56 ml of benzene and 20 ml of hexane and further from a mixed solvent of 91 ml of benzene and 39 ml of hexane to obtain 15.56 g (0.045 mol) of (−)-1/(−)-3 salt. m.p. 101°–102° C. The yield based on the employed (−)-1 was 63%. 54 ml of a 1N sodium hydroxide solution was added to the salt, followed by ether extraction. 72 ml of 1N hydrochloric acid was added to the resulting aqueous layer, which was then extracted with ether. The organic layer was dried over anhydrous sodium sulfate and ether was distilled away to obtain 7.86 g (0.0437 mol) of (−)-1. Yield 61%, $[\alpha]_{589} = -8.58°$ (C=1.0, 99% ethanol), optical purity 99%.

EXAMPLE 9

18.0 g (0.1 mol) of (±)-1, 8.1 g (0.06 mol) of (±)-2 and 1.6 g (0.04 mol) of sodium hydroxide were dissolved in 50 g of water at 72° C. After being allowed to cool overnight, the deposited crystals were separated by filtration to obtain 11.9 g (0.038 mol) of (−)-1/(+)-2 salt. The yield based on the used (−)-1 was 75%. 40 ml of 1N sodium hydroxide solution was added to the salt, followed by ether extraction. The ether layer was dried over anhydrous sodium sulfate and the solvent as distilled away under reduced pressure to obtain 6.3 g (0.035 mol) of (−)-1. The HPLC analysis of this compound gave (−)-1/(+)-1 =98.5/1.5. Optical purity 97.0%.

HPLC condition
Column: BAKERBOND (COVALENT) CHIRL produced by J.T. BAKER RESEARCH PRODUCT
(2 columns in series)
Mobile phase: n-hexane/isopropanol =1980/20
Flow rate: 1.0 ml/min
Temperature: 3° C.

EXAMPLE 10

18.0 g (0.10 mol) of (±)-1, 8.1 g (0.06 mol) of (±)-2 and 2.7 g (0.04 mol) of 25% ammonia water were dissolved in 50 g of water at 80° C. After being allowed to cool overnight, the deposited crystals were separated by filtration to obtain 13.0 g (0.041 mol) of (−)-1/(±)2 salt. This salt was twice recrystallized from each 50 g of water to obtain 8.6 g (0.027 mol) of (−)-1/(+)-2 salt. The yield based on (−)-1 was 55%. 40 ml of a 1N sodium hydroxide solution was added to the salt, followed by ether extraction. The ether layer was dried over anhydrous sodium sulfate and the solvent was distilled away under reduced pressure to obtain 4.5 g (0.025 mol) of (−)-1. The analysis of this compound by HPLC under the same condition as in Example 9 gave (−)-1/(+)-1 =99.5/0.5. Optical purity 99.0%.

EXAMPLE 11

18.0 g (0.1 mol) of (±)-1, 6.7 g (0.05 mol) of (+)-2 and 2.0 g (0.05 mol) of sodium hydroxide were dissolved in 50 g of water at 67° C. After being allowed to cool overnight, the deposited crystal were separated by filtration to obtain 13.0 g (0.041 mol) of (−)-1/(+)-2 salt. The yield based on the used (−)-1 was 82%. 40 ml of 1N sodium hydroxide solution was added to the salt, followed by ether extraction. The ether layer was dried over anhydrous sodium sulfate and the solvent was distilled away under reduced pressure to obtain 7.0 g (0.039 mol) of (−)-1. Yield 78%. The HPLC analysis of this compound under the same conditions as in Example 9 gave (−)-1/(±)-1 =99.0/1.0. Optical purity 98.0%.

EXAMPLE 12

18.0 g (0.1 mol) of (±)-1, 6.7 g (0.05 mol) of (+)-2 and 2.0 g (0.05 mol) of sodium hydroxide were dissolved in 30 g of water at 68° C. After being allowed to cool overnight, the deposited crystals were separated by filtration to obtain 10.7 g (0.034 mol) of (−)-1/(+)-2 salt. The yield based on the used (−)-1 was 68%. 40 ml of 1N sodium hydroxide solution was added to the salt, followed by ether extraction. The ether layer was dried over anhydrous sodium sulfate and the solvent was distilled away under reduced pressure to obtain 5.8 g (0.032 mol) of (−)-1. Yield 64%. The HPLC analysis of this compound under the same conditions as in Example 9 gave (−)-1/(+)-1 =98.8/1.2. Optical purity 97.6%.

EXAMPLE 13

9.0 g (0.05 mol) of (±)-1, 4.95 g (0.03 mol) of (±)-3 and 0.8 g (0.02 mol) of sodium hydroxide were dissolved in 25 g of water at 50° C. After being allowed to cool overnight, the deposited crystals were separated by filtration to obtain 7.68 g (0.022 mol) of (−)-1/(−)-3 salt. The yield based on the used (−)-1 was 88%. 20 ml of 1N sodium hydroxide solution was added to the salt, followed by ether extraction. The ether layer was dried over anhydrous sodium sulfate and the solvent was distilled away under reduced pressure to obtain 3.6 g (0.02 mol) of (−)-1. Yield 80%. The HPLC analysis of this compound under the same conditions as in Example 9 gave (−)-1/(+)-1 =98.9/1.1. Optical purity 97.8%.

What is claimed is:

1. A process for the optical resolution of (±)-2-hydroxy-4-phenylbutanoic acid which comprises treating (-±)-2-hydroxy-4-phenylbutanoic acid with an optically active 1-(p-tolyl)ethylamine or an optically active N-(2-hydroxy)ethyl-α-methylbenzylamine as a resolving agent.

2. A process of claim 1 wherein the treatment is carried out in a solvent.

3. A process of claim 2 wherein said solvent is selected from the group consisting of $C_{1-6}$ alkanol, $C_{3-6}$ alkyl methyl ketone, unsaturated or methyl- or ethyl-substituted benzene, $C_{6-8}$ cycloalkane, $C_{6-10}$ alkane, water, dioxane, tetrahydrofuran and tetrahydroyran and a mixture thereof.

4. A process of claim 3 wherein said solvent is selected, when optically active 1-(p-tolyl)ethylamine is used as the resolving solvent, from the group consisting of water, dioxane and methyl isobutyl ketone, and when optically active N-(2-hydroxy)ethyl-α-methylberzylamine is used as the resolving solvent, from the group consisting of an unsubstituted methyl- or ethyl-substituted benzene, a $C_{6-8}$ cycloalkanes, a $C_{6-10}$ alkane and a mixture thereof, and water.

5. A process for the optical resolution of (±)-2-hydroxy-4-phenylbutanoic acid which comprises cooling a solution of (-±)-2-hydroxy-4-phenylbutanoic acid and an optically active 1-(p-tolyl)ethylamine or ar optically active N-(2-hydroxy)ethyl-α-methylbenzylamine as a resolving solvent in a solvent to deposit one of the resulting diastereomer salts, separating the deposited diastereomer salt and treating the salt with an acid to produce (+)- or (−)-2-2-hydroxy-4-phenylbutanoic acid.

6. (+)-1-(p-tolyl)ethylamine salt of (−)-2-hydroxy-4-phenylbutanoic acid.

7. (−)-N-(2-hydroxy)ethyl-α-methylbenzylamine salt of (−)-2-hydroxy-4-phenylbutanoic acid.

* * * * *